(12) United States Patent
Fukakusa

(10) Patent No.: US 8,803,114 B1
(45) Date of Patent: Aug. 12, 2014

(54) ION GENERATION UNIT

(75) Inventor: Hiroyuki Fukakusa, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 0 days.

(21) Appl. No.: 14/118,932

(22) PCT Filed: Apr. 26, 2012

(86) PCT No.: PCT/JP2012/061225
§ 371 (c)(1),
(2), (4) Date: Nov. 20, 2013

(87) PCT Pub. No.: WO2012/160942
PCT Pub. Date: Nov. 29, 2012

(30) Foreign Application Priority Data

May 26, 2011 (JP) ................................. 2011-117700

(51) Int. Cl.
*H01T 4/12* (2006.01)
*H01J 27/02* (2006.01)

(52) U.S. Cl.
CPC .................................... *H01J 27/022* (2013.01)
USPC .................................... 250/515.1; 250/423 R

(58) Field of Classification Search
USPC ................. 250/515.1, 505.1, 423 R
See application file for complete search history.

(56) References Cited

U.S. PATENT DOCUMENTS 3,176,447 A * 4/1965 Omohundro et al. ........... 96/224
2001/0046822 A1 11/2001 Yoshikawa et al.

FOREIGN PATENT DOCUMENTS

| JP | 60-166200 U | 11/1985 |
| JP | 2000-323884 A | 11/2000 |
| JP | 2006-127855 A | 5/2006 |
| JP | 2009-266664 A | 11/2009 |

OTHER PUBLICATIONS

Official Communication issued in International Patent Application No. PCT/JP2012/061225, mailed on Aug. 7, 2012.

* cited by examiner

*Primary Examiner* — Kiet T Nguyen
(74) *Attorney, Agent, or Firm* — Keating & Bennett, LLP

(57) ABSTRACT

An ion generation unit (1) provided with an ion generation element (20) for generating ions through application of voltage, and a casing (10) housing the ion generation element. The casing is constituted by a casing body (11) and a rear cover (12). To the inside face of the casing are attached suppressing members (30, 31, 32, 33) for suppressing the radiation noise associated with ion generation. Openings (13, 14) through which the ions generated by the ion generation element are emitted to the outside are formed in the casing body, and the suppressing members are attached at locations other than the openings.

2 Claims, 4 Drawing Sheets

ION GENERATION UNIT

TECHNICAL FIELD

The present invention relates to an ion generation unit.

BACKGROUND ART

In recent years, there are many electric apparatuses that generate one or both of positive ions and negative ions to obtain effects of germ eradication, deodorization, refreshing and the like. An air conditioner, an air cleaner, a dehumidifier and the like are typical electric apparatuses with which an ion generation apparatus is combined. Some are put in the market as stand-alone ion generation apparatuses.

A traditional method to generate ions is corona discharge. In this method, a high voltage is applied to a discharge body in the atmosphere to produce corona discharge, thereby generating ions electrically. Patent document 1 discloses an example of an ion generation apparatus that uses the corona discharge.

The ion generation apparatus disclosed in the patent document 1 steps up an input voltage from a commercial power supply by means of a voltage step-up apparatus, further transforms it into a drive voltage that has a predetermined drive waveform, then applies it to the ion generation device to generate positive ions and negative ions.

CITATION LIST

Patent Literature

PLT1: JP-A-2006-127855

SUMMARY OF INVENTION

Technical Problem

According to its operation principle, an ion generation apparatus requires switching at a high voltage and cannot evade occurrence of a radiant noise caused by the switching. As anti-radiant-noise measures, the following measures are employed:
  (a) Lowering the peak value of an ion generation voltage of the ion generation apparatus.
  (b) Enclosing a voltage step-up transformer with a shield case.
  (c) Attaching an adhesive tape (hereinafter "metal-foil tape" in the present specification) containing a metal (usually aluminum) foil as a component, to an outer surface of the ion generation device.

In the ion generation apparatus disclosed in the patent document 1, a measure mainly following the lead of above measure (b) is adopted. Namely, a copper tape, a kind of metal-foil tape, is wound around a voltage step-up coil, and a shield case formed of a tin plate is disposed around the voltage step-up coil to curb occurrence of a radiant noise.

According to the above measure (a), a voltage applied to a discharge body declines and it becomes hard to generate intended amount of ions. Also the measure (b) has the same problem as the measure (a) that the voltage applied to the discharge body declines. This is because a discharge occurs between a secondary terminal of the voltage step-up transformer and the shield case.

In a case of taking the above measure (c), a degree of radiant noise curbing changes depending on the manner how the metal-foil tape is attached. It is possible to look for, through trial and error, a way of metal-foil tape attachment that curbs the radiant noise and does not reduce the amount of generated ions so much. However, this method requires preparation of ion generation devices, to which the metal-foil tape has been attached, as service parts. Besides, an acceptable level of radiant noise depends on the type of electric apparatuses into which the ion generation device is incorporated, and it is necessary to provide, as service parts, many kinds of ion generation devices having the metal-foil tape attached in different ways.

The present invention has been made in light of the above points, and it is an object to provide an ion generation unit that reduces a radiant noise to improve the reliability of a product without reducing an amount of generated ions, and further does not require many kinds of ion generation devices as service parts.

Solution to Problem

An ion generation unit according to the present invention includes: an ion generation device that generates ions by voltage application; and a casing that houses the ion generation device; wherein an inner surface of the casing is provided with a curbing member that curbs a radiant noise caused by ion generation.

In the ion generation unit having the above structure, it is preferable that the casing is provided with an opening portion that discharges the ions generated from the ion generation device to outside, and a portion other than the opening portion is provided with the curbing member.

In the ion generation unit having the above structure, it is preferable that the curbing member is composed of a metal plate.

In the ion generation unit having the above structure, it is preferable that the curbing member is composed of an adhesive sheet that contains a metal foil as a component.

Advantageous Effects of Invention

According to the present invention, the inner surface of the casing that houses the ion generation device is provided with the curbing member that curbs the radiant noise: accordingly, it is possible to reduce the radiant noise without reducing an amount of generated ions. Besides, the ion generation device is not modified: accordingly, it is unnecessary to prepare many kinds of the ion generation devices as service parts.

DESCRIPTION OF EMBODIMENTS

Figure 1:
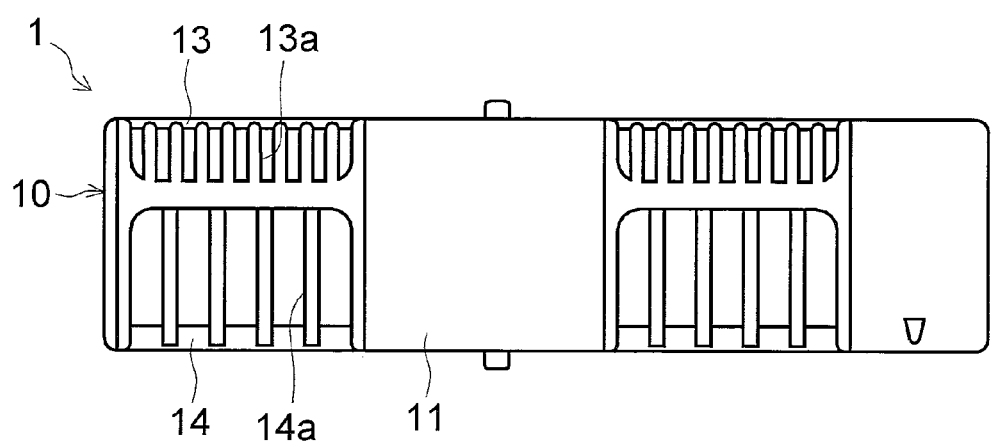
FIG. 1 is a front view of an ion generation unit according to an embodiment of the present invention.

An ion generation unit 1 as an embodiment of the present invention is designed as a unit to be incorporated in other apparatuses such as, for example, an indoor unit of an air conditioner, an air cleaner, a car and the like. The ion generation unit 1 includes a synthetic resin casing 10 that has a shape of a small-sized indoor unit of an air conditioner and is laterally long. The casing 10 includes a casing main body 11 and a rear lid 12 (see FIG. 3). The rear lid 12 is visible from a rear side only, and when viewed from a front side, the casing main body 11 makes up an entire appearance. In the meantime, an upper side and a lower side of FIG. 1 correspond to an upper side and a lower side of the ion generation unit 1, respectively, and a left side and a right side of FIG. 1 correspond to a left side and a right side of the ion generation unit 1, respectively. This orientation also applies to other components.

An ion generation device 20 is housed in the casing 10. The ion generation device 20 has a rectangular parallelepiped shape. When applied a predetermined voltage to the ion generation device 20, the ion generation device 20 generates ions by corona discharge. The ion generation device 20 is able to generate positive ions $H^+(H_2O)_m$ (m is an arbitrary natural number) and negative ions $O_2^- (H_2O)_n$ (n is an arbitrary natural number) concurrently.

The casing main body 11 is provided with opening portions at a position near the left end and at a position near the right end, through both of which ions generated by the ion generation device 20 are discharged. The positions of the opening portions correspond to positions of ion generation portions (not shown) of the ion generation device 20. Both the left opening portion and the right opening portion are formed by arranging an opening portion 13 that extends from the front surface to an upper surface of the casing main body 11 and an opening portion 14 that extends from the upper surface to a lower surface of the casing main body 11 vertically. The opening portions 13, 14 are provided with sets of a plurality of vertical crosspieces at predetermined intervals that prevent foreign matter from entering the casing 10. Crosspieces 13a are arranged at relatively narrow intervals in the opening portion 13 while crosspieces 14a are arranged at relatively wide intervals in the opening portion 14.

Figure 2:
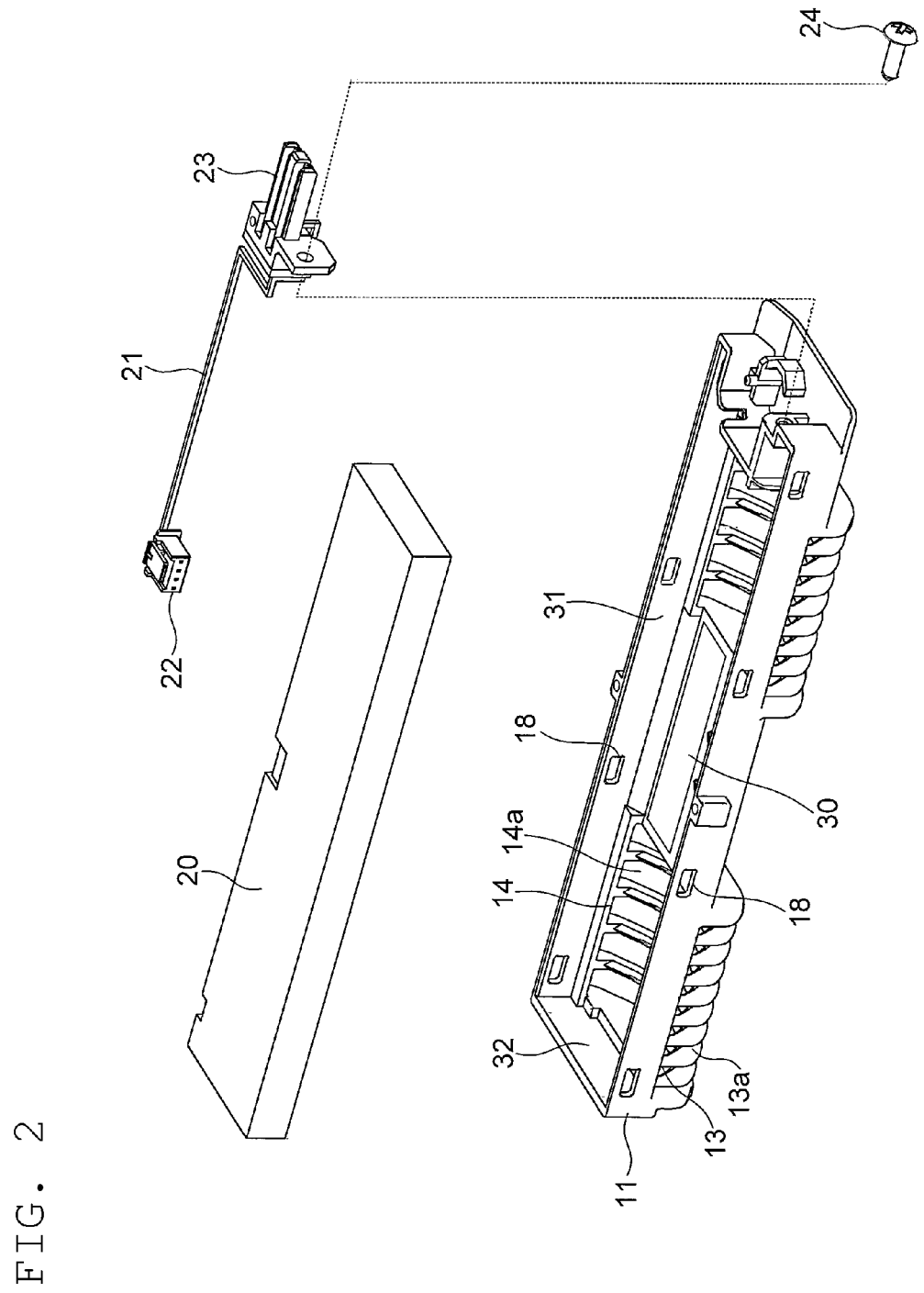
FIG. 2 is an exploded perspective view of components.

As shown in FIG. 2, the casing main body 11 is placed on an assembly table or the like with the front surface thereof down and the rear opening thereof, into which the rear lid 12 is fitted, up. The ion generation device 20 is inserted into the casing main body 11 through the rear opening. A power supply cable 21 is connected to the ion generation device 20. The power supply cable 21 has connectors 22, 23 at both ends. The connector 22 is to be connected to the ion generation device 20, while the connector 23 is to be connected to an external power supply cable (not shown). The connector 23 is fixed to the casing main body 11 by means of a screw 24.

Figure 3:
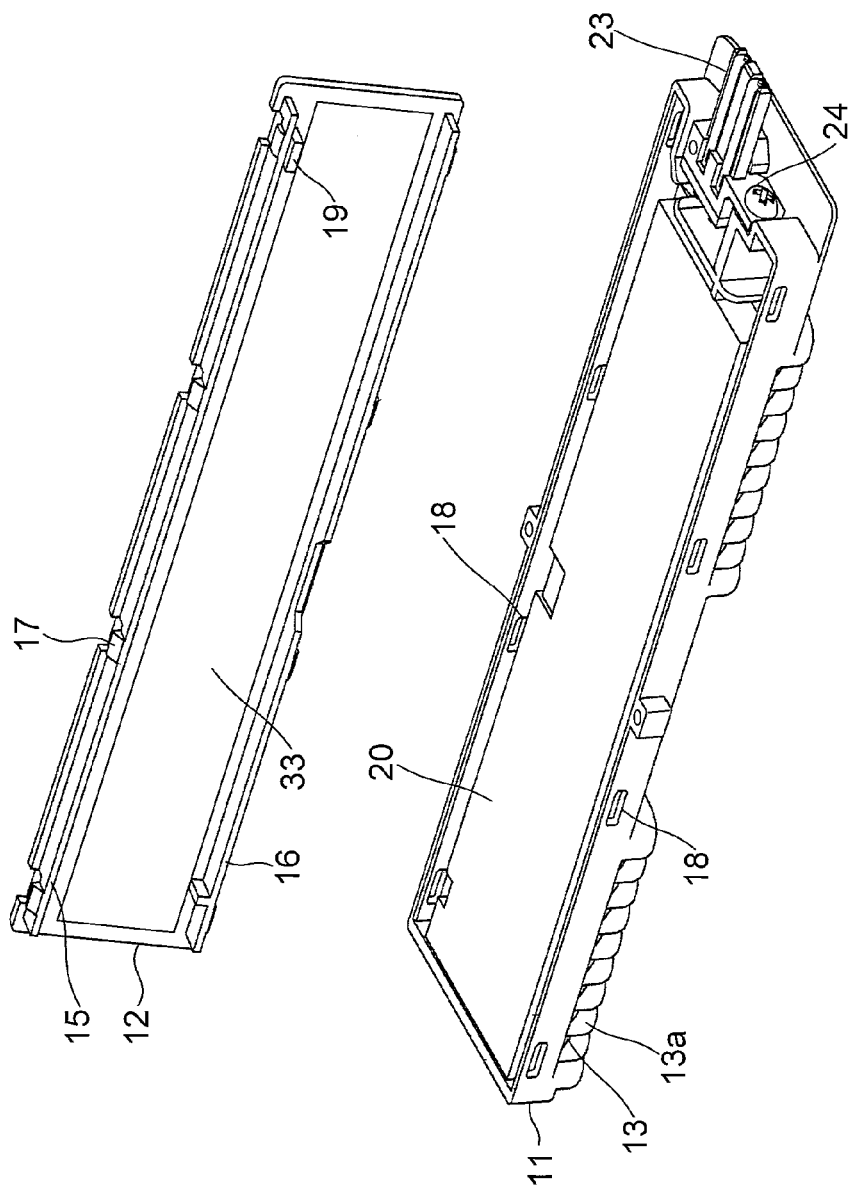
FIG. 3 is a perspective view of an ion generation unit in an assembled state to which a rear lid is ready to be fitted.

As shown in FIG. 3, when the rear lid 12 is fitted with the ion generation device 20 and the power supply cable 21 set in the casing main body 11, the ion generation unit 11 reaches completion. As to the rear lid 12, a surface facing an inside of the casing 10 is provided with two stripes of protrusions 15, 16 that go into an internal space of the casing main body 11. Both protrusions 15 and 16 extend in a horizontal direction. The protrusion 15 is formed at a position that is lower than an upper edge of the rear lid 12 by a thickness of an outer shell of the casing main body 11, while the protrusion 16 is formed at a position that is higher than a lower edge of the rear lid 12 by the thickness of the outer shell of the casing main body 11.

An upper surface of the protrusion 15 and a lower surface of the protrusion 16 are each provided with a plurality of engagement protrusions 17. In the embodiment, the protrusion 15 is provided with four engagement protrusions 17, and also the protrusion 16 is provided with four engagement protrusions 17 at an equal interval. In the meantime, the number "four" defining protrusion quantity is a mere example and does not limit the invention. The casing main body 11 is provided with a plurality of engagement holes 18 at positions corresponding to the engagement protrusions 17.

Figure 4:
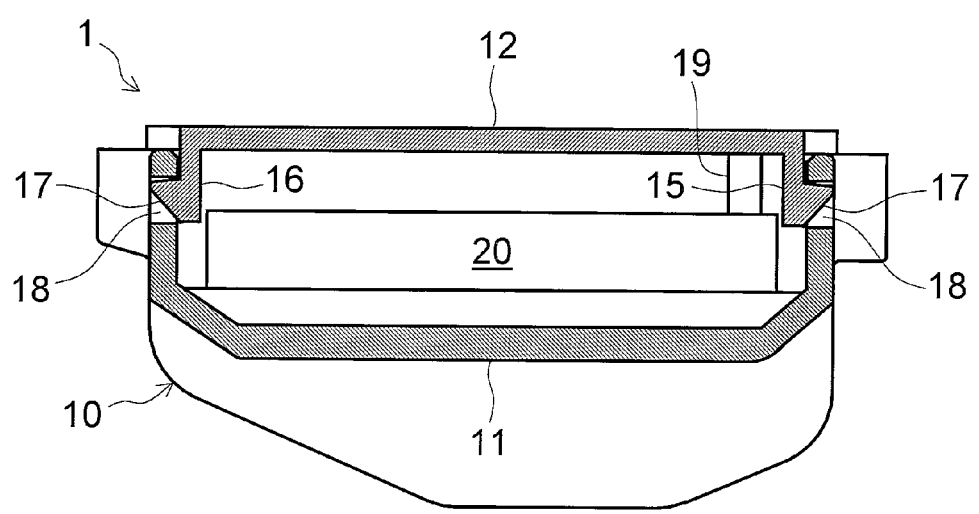
FIG. 4 is a sectional view of an ion generation unit.

When the rear lid 12 is placed on the casing main body 11 in the state of FIG. 3 and a downward force is exerted on the rear lid 12, the engagement protrusion 17 engages with the engagement hole 18 to go to a state shown in FIG. 4. In this state, protrusions 19 formed at some positions of an inner surface of the rear lid 12 push down the ion generation device 20, whereby the ion generation device 20 is firmly fixed.

An inner surface of the casing 10 is provided with a curbing member that curbs a radiant noise caused by the ion generation. The curbing member can be composed of a metal plate. The metal plate can be fixed to the casing 10 by means of an adhesive, a double-faced adhesive tape, a screw or the like.

The curbing member can be composed of an adhesive sheet that contains a metal foil, an aluminum foil for example, as a component. Such a curbing member is easy to mount. If the adhesive sheet is formed into a roll of adhesive tape, it becomes easy to handle.

It is preferable to mount the curbing member on both the casing main body 11 and the rear lid 12. FIG. 2 shows a state where the curbing member is mounted on an inner surface of the casing main body 11. The curbing member 30 is mounted on a flat inner surface between the left and right opening portions 13, 14, the curbing member 31 is mounted on a lower inner surface, and the curbing member 32 is mounted on a left inner surface. A curbing member, which pairs with the curbing member 31, is mounted on an upper inner surface that is hidden in FIG. 2. Likewise, a curbing member, which pairs with the curbing member 32, is mounted on a right inner surface that is hidden in FIG. 2.

FIG. 3 shows a state where a curbing member is mounted on the inner surface of the rear lid 12. The curbing member 33 covers a flat portion between the protrusions 15, 16.

As described above, the curbing members 30, 31, 32, and 33 are mounted on the inner surface of the casing main body 11: accordingly, it is possible to reduce the radiant noise without mounting a curbing member on the ion generation device 20. The curbing members 30, 31, 32, and 33 are mounted on places other than the opening portions 13, 14: accordingly, discharge of the ions through the opening portions 13, 14 is not discouraged, i.e. an amount of discharged ion is not reduced.

The ion generation device 20 is not modified: accordingly, it is unnecessary to prepare many kinds of the ion generation devices 20 as service parts. In other words, the ion generation device 20 is standardizable.

In various apparatuses that incorporate the ion generation unit 1, the structure of a holder that holds the ion generation unit 1 is unique to each apparatus. However, even if an apparatus is modified, as long as the holder structure is the same, the same ion generation unit 1 is incorporable. In other words, the same ion generation device 20 as a standard service part is usable.

Hereinbefore, the embodiment of the present invention is described. However, the scope of the present invention is not limited to the embodiment, and various modifications can be made if the modifications do not depart from the spirit of the invention.

INDUSTRIAL APPLICABILITY

The present invention is widely applicable to ion generation units.

REFERENCE SIGNS LIST 1 ion generation unit
2 casing
11 casing main body
12 rear lid
13, 14 opening portions 20 ion generation device
30, 31, 32, 33 curbing members

The invention claimed is:

1. An ion generation unit comprising:
an ion generation device that generates ions by voltage application;
a resin casing that houses the ion generation device; and
a curbing member that curbs a radiant noise caused by ion generation; wherein
the casing is provided with a first and a second opening portions that are arranged away from each other in a left-right direction, the ions generated from the ion generation device are discharged through the first and the second opening portions;
the curbing member is composed of a metal plate or includes a metal foil; and
the curbing member is mounted on an inner surface of a portion between the first and second opening portions of the casing.

2. The ion generation unit according to claim 1, wherein the curbing member is composed of an adhesive sheet that contains the metal foil as a component.

* * * * *